US012636054B2

(12) United States Patent     (10) Patent No.:   US 12,636,054 B2

Biedermann et al.     (45) Date of Patent:    May 26, 2026

---

(54) BONE ANCHOR

(71) Applicant: BIEDERMANN TECHNOLOGIES GMBH & CO. KG, Donaueschingen (DE)

(72) Inventors: Timo Biedermann, Trossingen (DE); Berthold Dannecker, St. Georgen (DE); Bernd Fischer, Bräunlingen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 566 days.

(21) Appl. No.: 18/165,168

(22) Filed: Feb. 6, 2023

(65) Prior Publication Data

US 2023/0248408 A1     Aug. 10, 2023

Related U.S. Application Data

(60) Provisional application No. 63/307,268, filed on Feb. 7, 2022.

(30) Foreign Application Priority Data

Feb. 7, 2022    (EP) ..................................... 22155488

(51) Int. Cl.
     *A61B 17/86*      (2006.01)
(52) U.S. Cl.
     CPC ................................. *A61B 17/863* (2013.01)
(58) Field of Classification Search
     CPC .................................................. A61B 17/863
     See application file for complete search history.

(56) References Cited

U.S. PATENT DOCUMENTS

| | | | |
|---|---|---|---|
| 5,120,171 A | 6/1992 | Lasner | |
| 9,055,986 B1 * | 6/2015 | Whipple | ............ A61B 17/8635 |
| 10,188,430 B2 | 1/2019 | Sauvage et al. | |
| 10,531,904 B2 | 1/2020 | Kolb | |

(Continued)

FOREIGN PATENT DOCUMENTS

| | | |
|---|---|---|
| DE | 20 2012 002 636 U1 | 2/2013 |
| FR | 3 102 924 A1 | 5/2021 |

OTHER PUBLICATIONS

Extended European Search Report for Application No. 22155488.4, mailed Jul. 20, 2022, 10 pages.

*Primary Examiner* — Olivia C Chang

(74) *Attorney, Agent, or Firm* — Womble Bond Dickinson (US) LLP

(57)      ABSTRACT

A bone anchor includes a shank with a first end, an opposite second end, and a longitudinal axis. The shank includes a core, a thread that extends in a helix around the core and that has a lower flank directed towards the first end and an upper flank directed towards the second end, wherein the upper flank and the lower flank define a first cross-sectional thread shape, and an additional thread structure including a recess that extends together with part of the thread in the helix around the core. The thread and the additional thread structure together define a second cross-sectional thread shape different from the first cross-sectional thread shape. An axial length of the portion of the thread that has only the first cross-sectional thread shape is greater than an axial length of the entire portion of the thread that includes the second cross-sectional thread shape.

20 Claims, 11 Drawing Sheets

(56) References Cited

U.S. PATENT DOCUMENTS

| | | | |
|---|---|---|---|
| 10,595,916 | B2 | 3/2020 | Hopkins |
| 2008/0249579 | A1 | 10/2008 | Taylor |
| 2011/0276095 | A1 | 11/2011 | Bar et al. |
| 2012/0232600 | A1 | 9/2012 | Wen et al. |
| 2013/0253596 | A1 | 9/2013 | Crook et al. |
| 2014/0121703 | A1 | 5/2014 | Jackson et al. |
| 2014/0277190 | A1 | 9/2014 | Splieth et al. |
| 2014/0329202 | A1 | 11/2014 | Zadeh |
| 2014/0336709 | A1 | 11/2014 | Avidano et al. |
| 2018/0325570 | A1 | 11/2018 | Kuntz et al. |

* cited by examiner

BONE ANCHOR

CROSS-REFERENCE TO RELATED APPLICATION(S)

The present application claims priority to and the benefit of U.S. Provisional Patent Application No. 63/307,268, filed Feb. 7, 2022, the contents of which are hereby incorporated by reference in their entirety, and claims priority from European Patent Application EP 22 155 488.4, filed Feb. 7, 2022, the contents of which are hereby incorporated by reference in their entirety.

BACKGROUND

Field

The application relates to a bone anchor which is particularly applicable in the field of orthopedic surgery.

Description of Related Art

In orthopedic surgery, bone anchors, such as bone screws, are used in a wide field of applications. For example, bone screws form part of polyaxial bone anchors that couple a rod to pedicles of vertebrae or that form part of bone plate assemblies. The bone screws are required to have sufficient mechanical performance to avoid loosening or inadvertent pull-out, as well as resistance against bending. Moreover, it is desirable that the bone screws allow for ingrowth of bone and tissue.

US 2011/0276095 A1 describes an orthopedic screw having a thread with two parts, a distal part and a proximal part, each having a different thread configuration. The distal section has a distal screw thread with an outer dimension and pitch suitable for entry into cancellous bone, while the proximal section has a double thread having a first screw thread having the same pitch and formed on the same helix as that of said distal screw thread, and a second screw thread having the same pitch but a smaller outer diameter than that of said distal screw thread and formed on a different helix. The screw is used in bone having a harder cortical outer section and a softer cancellous inner section.

U.S. Pat. No. 10,531,904 B2 describes a bone screw that includes a main body having a proximal end and a distal end, and that extends along a longitudinal axis. The main body has an externally threaded surface that includes at least one helically extending thread with two flank surfaces. The thread includes at least one aperture that extends along an aperture axis through the thread between the flank surfaces. The apertures provide space for the ingrowth of bone material.

SUMMARY

It is an object of the invention to provide an alternative and/or improved bone anchor that has improved mechanical performance.

A bone anchor according to an embodiment of the invention includes a shank configured to be anchored in bone, wherein the shank has a first end configured to be inserted first and an opposite second end, and a longitudinal axis extending through the first end and the second end, a core, and a thread configured to engage bone. The thread includes a number of turns of a helix around the core, the number of turns defining an axial length of the thread. A thread shape of the thread is defined at least by a lower flank facing towards the first end and an upper flank facing towards the second end. The shank further includes an additional thread structure with a modified thread shape along a portion of the core that is shorter than the axial length of the thread, wherein the additional thread structure has a recess that is at least partially helix-shaped.

By means of the additional thread structure, mechanical stress or tension may be generated between the flanks of the additional thread structure when the additional thread structure engages the bone. Preferably, the additional thread structure is provided at a position of the shank that remains in the cortical bone once the bone anchor has been fully inserted into bone. In the cortical bone, the additional thread structure may provide for an increased holding force and/or increased resistance against screwing back, loosening, or backing out of the bone anchor. The thread may be a single thread or a multiple thread, in particular, a double thread.

According to a specific embodiment, the additional thread structure may include a lower flank that is separated from the upper flank by an at least partially helix-shaped slit. Thereby, the lower flank may be slightly flexible towards the upper flank. This may create tension between the upper flank and the lower flank and the surrounding bone. In a further development, the lower flank of the additional thread structure may include a plurality of transverse slits that render the lower flank segmental. Such a segmental lower flank may enhance flexibility and/or the segments may act like barbs that can reduce the risk of loosening of the bone anchor or provide resistance against screwing out.

In a further specific embodiment, the additional thread structure has a modified thread shape that is thicker compared to the thread shape of the rest of the thread. Such a thicker thread may result in additional compression of the surrounding bone when the bone anchor is inserted.

According to a further embodiment, the at least partially helix-shaped recess of the additional thread structure forms an undercut that separates the upper and lower flanks of the additional thread structure at least partially from the core. Thereby, a slight flexibility of the additional thread structure may be achieved, which may result in tension created between the flanks of the additional thread structure and the bone.

According to a further embodiment, the additional thread structure includes a separate helix in between the helical turns of the thread. Moreover, the separate helix may have a section that is offset towards the second end of the shank. Thus, a ramp-like structure is created that may result in an additional compression of the surrounding material during screwing in and may account for an improved holding force of the bone anchor and reduces the risk of loosening or pull-out of the bone anchor.

According to a still further embodiment, the at least partially helix-shaped recess includes at least one aperture that extends from the upper flank through the thread turn to the lower flank and which is arranged inside the crest of the thread. Such aperture may improve the ingrowth of bone material.

In a still further embodiment, the at least partially helix-shaped recess includes at least one helical groove in the upper and/or the lower flank that extends along a portion of the helix of the thread. This may also improve the ingrowth of bone material.

Still further embodiments may combine the various additional thread structures.

Compared to the thread shape of the thread (i.e., the primary or traditional thread), the additional thread structure includes complex deviations from this shape. Such deviations may include recesses and/or an addition of material. When using a subtractive manufacturing technology, in particular, the manufacturing of undercuts becomes difficult. Therefore, the bone anchor is advantageously manufactured by an additive manufacturing method, such as laser sintering or laser melting, electron beam melting, or any other suitable three-dimensional printing technique. This allows for easier manufacturing of arbitrary complex shapes. As a result, a suitable additional thread structure may be designed according to the particular needs of a patient, and may also be easily manufactured on demand.

A particular field of application of the bone anchor is orthopedic surgery, more particularly, spine surgery. The bone anchor can be, for example, part of a monoaxial or polyaxial pedicle screw that is configured to connect the vertebra to a spinal rod. However, the bone anchor can also be used in other fields of spine and orthopedic surgery, for example, in connection with additional fixation of interbody cages, bone plates for osteosynthesis, or fixation of joint replacements.

BRIEF DESCRIPTION OF THE DRAWINGS

Further features and advantages of the invention will become apparent from the description of embodiments by means of the accompanying drawings. In the drawings:

FIG. 4a shows a side view of the bone anchor according to the first embodiment.

FIG. 4b shows an enlarged view of a detail of FIG. 4a.

FIG. 5a shows a cross-sectional view of the bone anchor according to FIGS. 4a and 4b, wherein the cross-section is taken in a plane including the shank axis and extending through a center of a head of the bone anchor.

FIG. 5b shows an enlarged view of a detail of FIG. 5a.

FIG. 7b shows an enlarged view of a detail of FIG. 7a.

FIG. 8b shows an enlarged view of a detail of FIG. 8a.

FIG. 9a shows a perspective view of a bone anchor according to a third embodiment.

FIG. 9b shows an enlarged view of a detail of FIG. 9a.

FIG. 10 shows an enlarged view of a portion of the bone anchor of FIG. 9a including a head, wherein the bone anchor is rotated compared to the view in FIG. 9a.

FIG. 11a shows a side-view of the bone anchor of FIGS. 9a to 10.

FIG. 11b shows an enlarged view of a detail of FIG. 11a.

FIG. 12a shows a cross-sectional view of the bone anchor of FIGS. 9a to 11b, wherein the cross-section is taken in a plane including the shank axis and extending through the center of the head.

FIG. 12b shows an enlarged view of a detail of FIG. 12a.

FIG. 14b shows an enlarged view of a detail of FIG. 14a.

FIG. 15b shows an enlarged view of a detail of FIG. 15a.

FIG. 16b shows an enlarged perspective view of a detail of FIG. 16a.

FIG. 17b shows an enlarged view of a detail of FIG. 17a.

FIG. 18a shows a perspective view of a bone anchor according to a sixth embodiment.

FIG. 18b shows an enlarged view of a detail of FIG. 18a.

FIG. 19a shows a cross-sectional view of the bone anchor of FIGS. 18a and 18b, the cross-section taken in a plane including the shank axis and extending through a center of a head of the bone anchor.

FIG. 19b shows an enlarged view of a detail of FIG. 19a.

DETAILED DESCRIPTION

Figure 1:
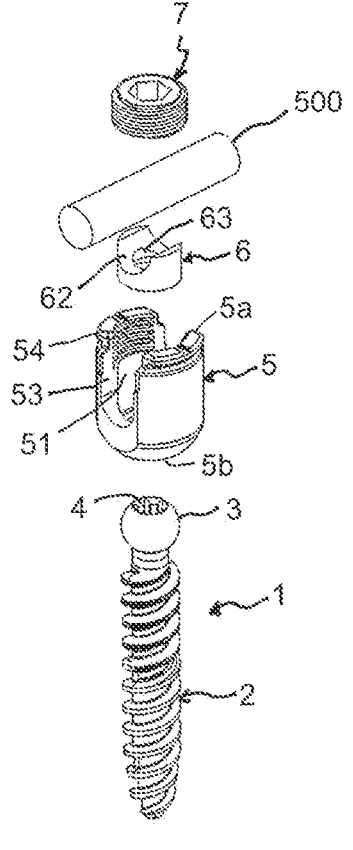
FIG. 1 shows a perspective exploded view of a polyaxial bone anchoring device including a bone anchor according to a first embodiment.
Figure 2:
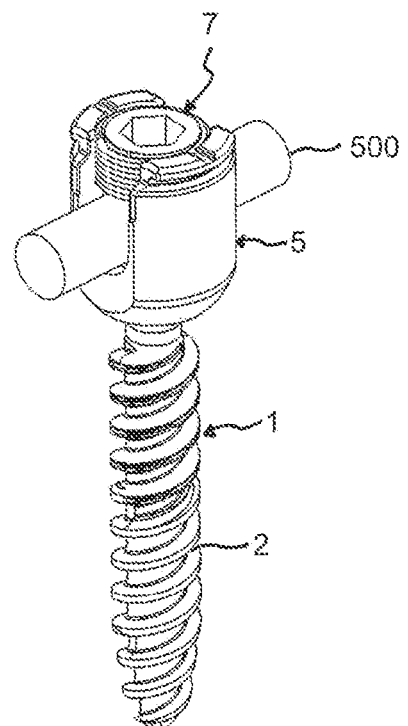
FIG. 2 shows a perspective view of the polyaxial bone anchoring device of FIG. 1 in an assembled state.
Figure 3:
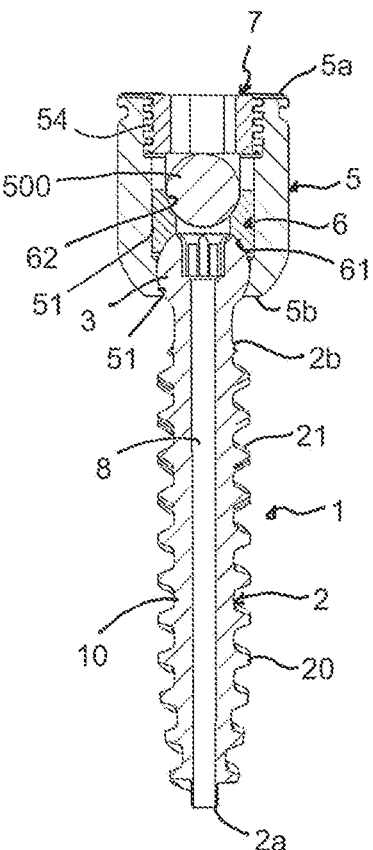
FIG. 3 shows a cross-sectional view of the polyaxial bone anchoring device of FIGS. 1 and 2, wherein the cross-section is taken in a plane perpendicular to an inserted rod.
Figures 4A, 4B, 5A, 5B:
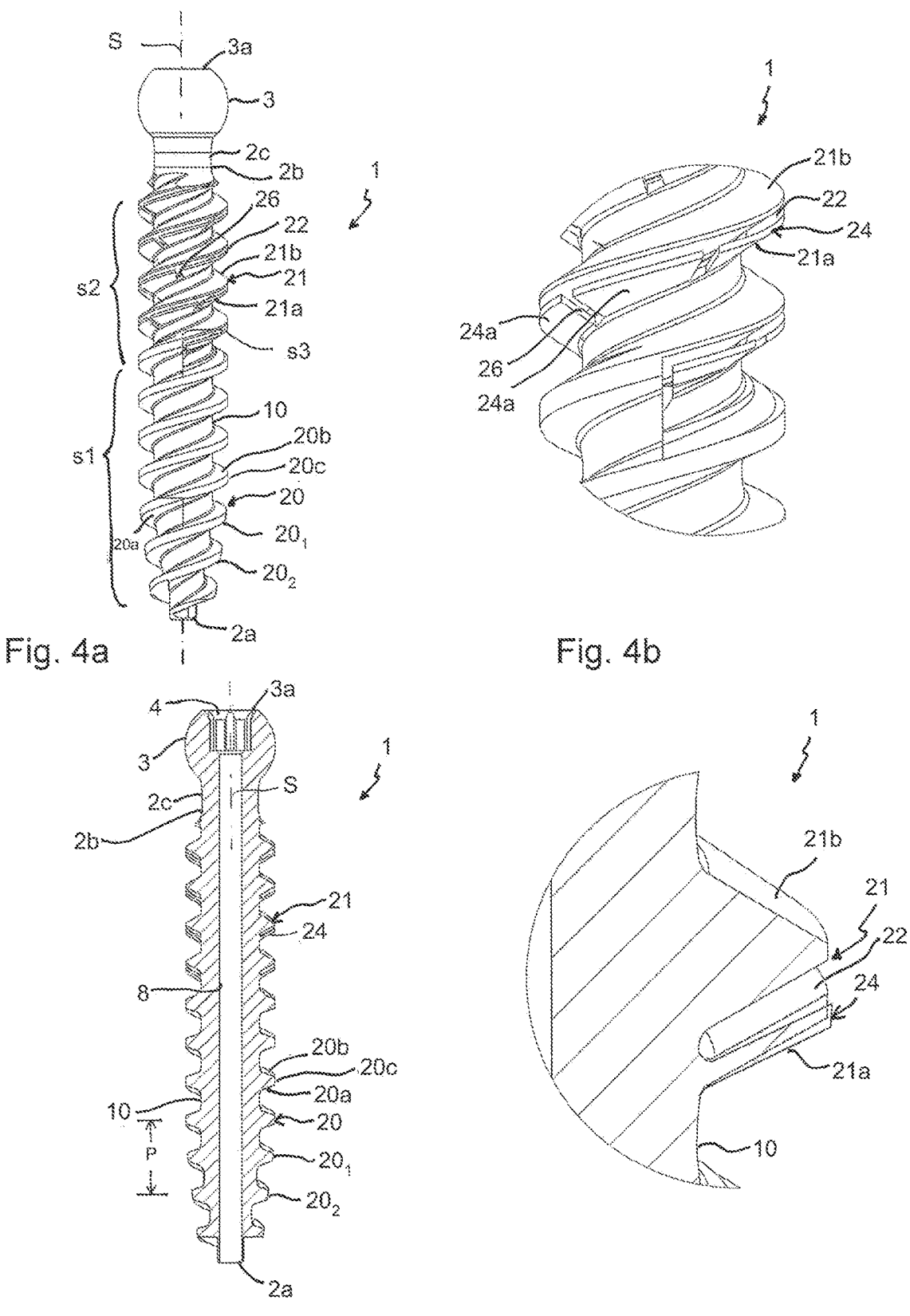
Figure 6:
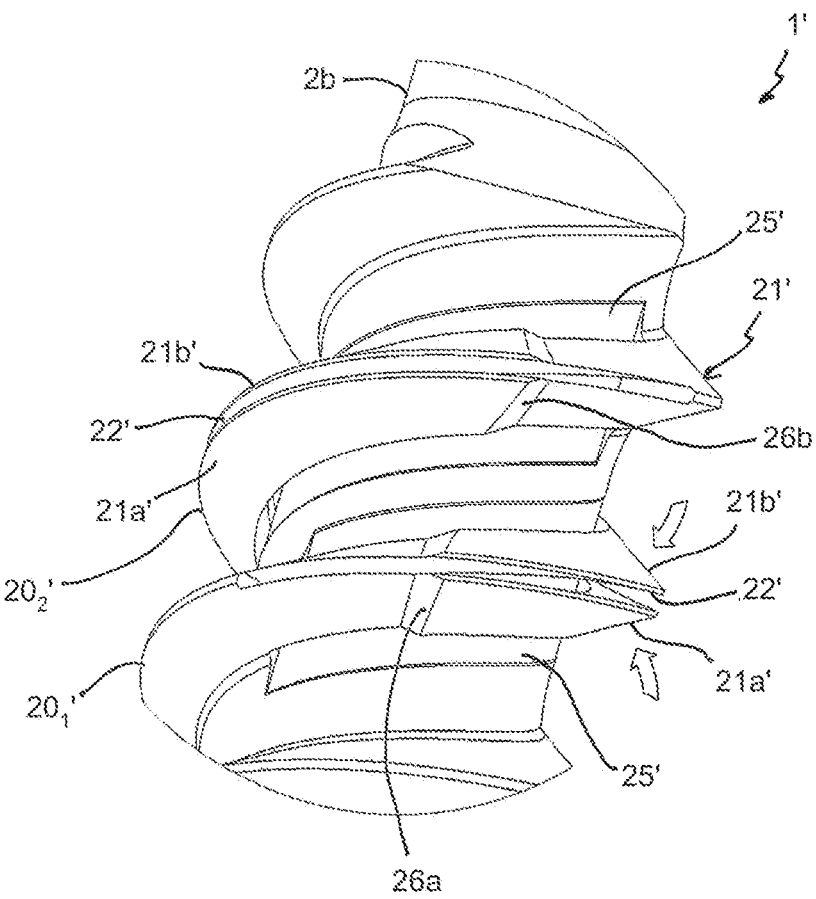
FIG. 6 shows an enlarged perspective view of a portion of a shank of a bone anchor according to a second embodiment.

Referring to FIGS. 1 to 3, a first embodiment of the bone anchor 1 is shown as a part of a polyaxial bone anchoring device. The bone anchor 1 includes a shank 2 to be anchored in bone, and a head 3 at a free end of the shank 2. The head 3 may have a recess 4 configured for engagement with a screwing-in tool. A receiving part 5 of the polyaxial bone anchoring device is configured to receive the head 3 of the bone anchor and a rod 500 in a manner such that the head 3 can pivot within the receiving part to assume various angular positions with respect to the receiving part 5 and the inserted rod 500. The polyaxial bone anchoring device further includes a pressure member 6 for exerting pressure onto the head 3 to lock the head 3 within the receiving part 5. A locking device 7, which may be a set screw, is configured to cooperate with the receiving part 5 and to press onto the rod 100 to fix the rod, which in turn transfers the pressure onto the pressure member 6 to lock the head 3 in the receiving part 5.

The receiving part 5 has a first or upper end 5a and an opposite second or lower end 5b, and a passage 51 extending from the first end 5a to the second end 5b. Adjacent to the second 5b, a seat 52 that may have a substantially spherical shape is provided for pivotably receiving the head 3 therein. The rod 500 can be inserted into a channel 53 formed by a substantially U-shaped recess extending from the first end 5a to a distance from the second end 5b. Adjacent to the first end 5a, an internal thread 54 may be provided in the receiving part 5 so that the locking device 7 can be screwed into the receiving part 5. The pressure member 6 is adapted to move within the passage 51 of the receiving part, and has a substantially spherical recess 61 on its side facing the inserted head 3 that is configured to contact the spherical outer surface portion of the head 3. On the opposite side, a substantially cylinder segment-shaped recess 62 is formed for providing a support surface for the rod 500. A coaxial hole 63 provides access for a tool to the head 3 when the head 3 is held in the receiving part.

It shall be noted that the bone anchor 1 is not limited to use with the polyaxial bone anchoring device described above. The bone anchor can also be combined with various other receiving parts with different designs, and with various other pressure members, locking devices, and/or rods from those shown in the figures.

As further shown in FIGS. 4a to 5b, the shank 2 has a first end 2a that is configured to enter the bone first, and an opposite second end 2b. At the first end 2a, a tip may be formed that may be blunt or sharp. Adjacent to the second end 2b of the shank 2, a neck 2c with a reduced outer diameter may be provided that continues into the head 3. The head 3 preferably has a spherical outer surface portion, in particular, the head 3 may have the shape of a spherical segment with a substantially flat end surface 3a. The entire bone anchor 1 may optionally be cannulated, with a channel 8 extending fully from the free end surface 3a of the head 3 through the shank 2 to the tip. The channel 8 is preferably coaxial with a shank axis S and has a circular cross-section. An inner diameter of the channel may be substantially constant over the length of the bone anchor or may vary along the length, and/or the cross-section may be other than circular.

The shank 2 includes a core 10 and a thread 20 winding in a helix around the core 10 in a plurality of turns. A central longitudinal axis S of the shank 2, which represents the shank axis, is also the screw axis of the thread 20. The core 10 may be cylindrical along most of the length of the shank 2. In greater detail, the core 10 may be cylindrical between the second end 2b and a distance from the first end 2a, with an outer diameter or core diameter that is the same or that may be greater than the outer diameter of the neck 2c. Also, the core 10 may taper in a region towards the first end 2a. In this embodiment, the thread 20 is a double thread that includes two thread entries, and therefore a first helix $20_1$ and a second helix $20_2$ that are offset axially and wind in an alternating manner around core 10. The helices $20_1$ and $20_2$ have the same pitch P, and the second helix $20_2$ runs in the middle between adjacent turns of the first helix $20_1$. Moreover, the thread entries of the double thread are offset by 180°. The thread pitch P and geometry of the thread 20 may be such that there is gap between the thread turns on the core 10. Generally, the thread shape and the thread pitch is such that the thread 20 is adapted to engage bone. A specific thread shape, the pitch, the number of threads, etc. are parameters that may depend on the type of bone into which the anchor is to be inserted and on the purpose of the bone anchor. The shank may also have thread free portions, i.e., the thread 20 may be present only in a portion or portions of the shank.

An axial length of the thread 20 preferably extends from the first end 2a of the shank 2 to the second end 2b. In a first axial thread section s1 adjacent to or close to the first end 2a, and preferably extending up to or beyond the middle of the shank 2, the thread 20 includes a plurality of turns. The shape of the thread 20 in the first thread section s1 is substantially defined at least by a lower flank 20a facing towards the first end 2a and an upper flank 20b facing towards the second end 2b of the shank 2. Between the lower flank 20a and the upper flank 20b, a substantially flat crest 20c of the thread 20 may be formed. In greater detail, parameters such as the shape of the flanks, the angle that the flanks form with each other, the thickness of the thread in the axial direction, and the cross-section of the thread may all contribute to define the thread shape. Generally, the thread shape of the thread 20 may have any shape that is configured to engage bone. For example, it can have a V-shape with a sharp, flat, or rounded crest. Thus, in this embodiment, the thread shape of the thread 20 in the thread section s1 can be referred to as a regular thread shape. In addition, in the first thread section s1, the thread 20 may run out towards the first end 2a. It shall be noted that the thread 20 may include cutting structures (not shown), for example, axial grooves, close to the first end or at a distance therefrom, which may slightly deviate from the regular shape of the thread 20.

In a second axial thread section s2 that is located closer to the second end 2b than to the first end 2a of the shank 2, an additional thread structure is provided. Preferably, the second axial thread section s2 is at a position such that the additional thread structure is configured to engage cortical bone when the bone anchor is fully inserted in bone. Thereby, the additional thread structure may increase the holding force that holds the bone anchor in the bone and/or may increase a resistance against loosening and/or pull-out of the bone anchor. In the embodiment, the additional thread structure includes a modified thread 21 that is modified with respect to the regular thread shape present in the first section s1. Preferably the modified thread 21 forms or makes up at least one turn of the helix.

The modified thread 21 forming the additional thread structure has an upper flank 21b facing towards the second end 2b of the shank 2 and a lower flank 21a facing towards the first end 2a of the shank 2. The upper flank 21b is coincident with the upper flank 20b of the thread 20. In other words, the upper flank 21b of the thread 21 has the same shape and size as the upper flank 20b of the thread 20, and merges continuously with the upper flank 20b of the thread 20 at a transition section s3 between the first section s1 and the second section s2. The lower flank 21a is shifted or offset axially towards the first end 2a as compared to the lower flank 20a of the thread 20 in the first section s1. Moreover, the lower flank 21a is separated from the upper flank 21b by a helical slit 22. By means of the slit 22, an additional helix 24 that includes the lower flank 21a is formed in the second thread section s2 for each of the helices $20_1$ and $20_2$. The additional helix 24 is shifted towards the first end 2a compared to the helix of the thread 20. By means of this, the thickness of the entire or combined thread in the axial direction in the second section s2 is increased compared to the regular thread shape in the first section s1. In the lower flank 21a, transverse slits 26 are formed that are open towards the outer free edge of the lower flank 21a. The transverse slits 26 form an angle with the shank axis S that may be the same as the flank angle of the lower flank 21a. By means of the slits 26, the additional helix 24 is divided into segments 24a. The thickness of the additional helix 24 in the axial direction is such that the additional helix 24 is flexible to some extent in the axial direction. In greater detail, the additional helix 24 is flexible against the remaining or other portions of the thread 21 in the second thread section s2. To achieve a desired flexibility, the number and/or width of the slits 26 can be selected accordingly. The position of the slits 26 along the additional helix 24 of the first helix $20_1$ and of the second helix $20_2$ of the thread are offset from each other. Thus, the segments 24a are also offset from each other from one turn to a next turn and/or from the first helix $20_1$ to the second helix $20_2$ when viewed in the axial direction.

In the embodiment, the second section s2 extends along an axial length that is only a little smaller than a half of the shank length. However, the second section is not restricted to such a length. In particular, the second section can have a length that includes at minimum a single turn of the additional helix 24, and at maximum extends up to a distance from the first end 2a that corresponds to a single turn of the thread 20.

The bone anchor may be made of any bio-compatible material, preferably however of titanium or stainless steel, or of any other bio-compatible metal or metal alloy or plastic material. For bio-compatible alloys, a NiTi alloy, for example Nitinol, may be used. Other materials that can also be used are magnesium or magnesium alloys. Bio-compatible plastic materials that can be used may be, for example, polyether ether ketone (PEEK) or poly-L-lactide acid (PLLA). The receiving part and other parts of the polyaxial bone anchoring device may be made of the same material or of different materials.

Preferably, the bone anchor is formed using an additive manufacturing method. In an additive manufacturing method, the bone anchor is built up layer-by-layer based on three-dimensional data that characterize the shape and size of the bone anchor. A preferred method is, for example, selective laser sintering or selective laser melting or electron beam melting, according to which successive layers of a powder material, for example stainless steel or titanium or another body compatible material, are sintered or melted at positions corresponding to the cross-section of the bone anchor in the respective layer, until the bone anchor is completed. With an additive manufacturing method, the additional thread structure is easily manufactured. Moreover, recesses that form undercuts and complex shapes can be built up. In the above embodiment, the manufacture of the additional helix 24 and the slit 26 can be made easily with such an additive method, whereas using a subtractive method would make it too difficult or even impossible to achieve such structures.

In use, the bone anchor 1 usually is inserted into a prepared core hole in the bone, for example, into the pedicle of a vertebra. The first thread section s1 is configured to be anchored in the softer cancellous bone. The second thread section s2 with the additional thread structure in the form of the modified thread 21 is configured to engage the harder cortical bone. During the insertion process and/or the final placement, the additional helix 24 is slightly compressed towards the upper flank 21b. Thereby, the upper flank 21b and the lower flank 21a are tensioned or pre-loaded against each other and in the bone. This can increase the holding force which holds the bone anchor in the bone. Furthermore, the segments 24a of the additional helix 24 can act as barbs that provide additional resistance against loosening, backing out, or inadvertent screwing-back of the bone anchor.

Figure 7A:
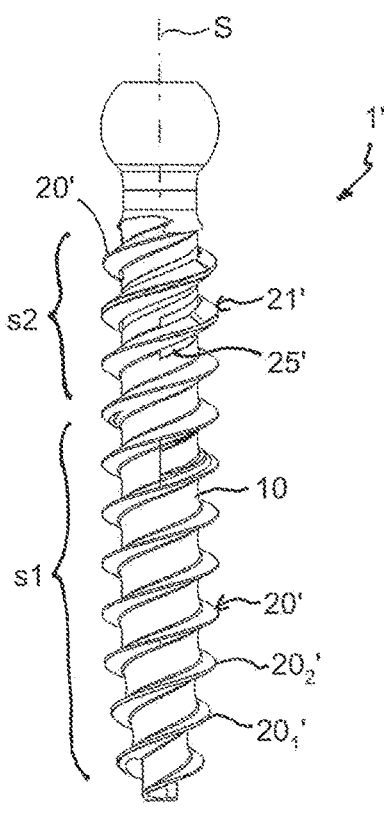
FIG. 7a shows a side view of the bone anchor according to the second embodiment.
Figure 7B:
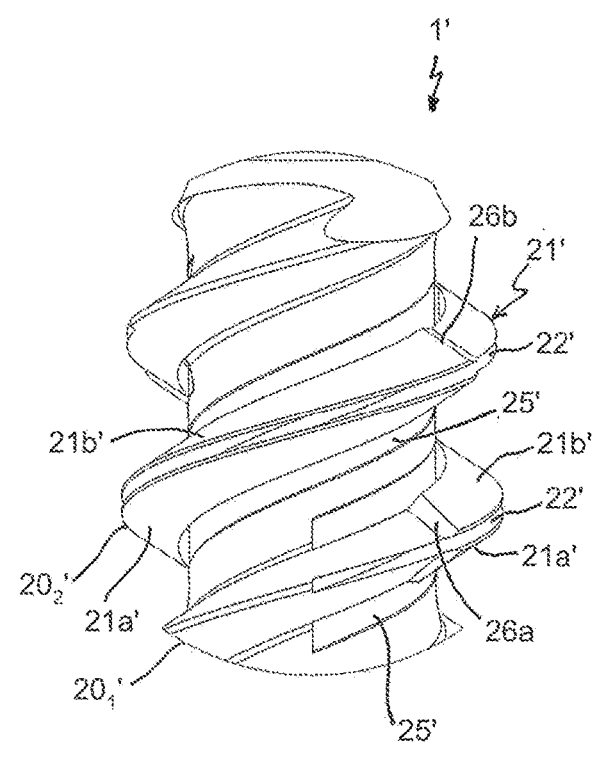
Figure 8A:
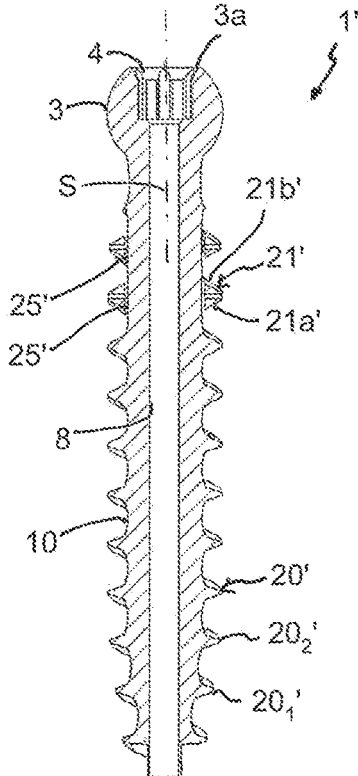
FIG. 8a shows a cross-sectional view of the bone anchor of FIGS. 6 to 7b, the cross-section taken in a plane including the shank axis and extending through a center of a head of the bone anchor.
Figure 8B:
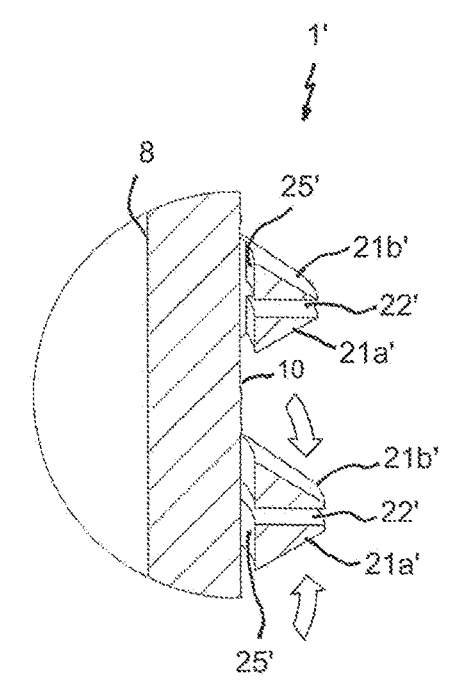
Figures 9A, 9B, 10:
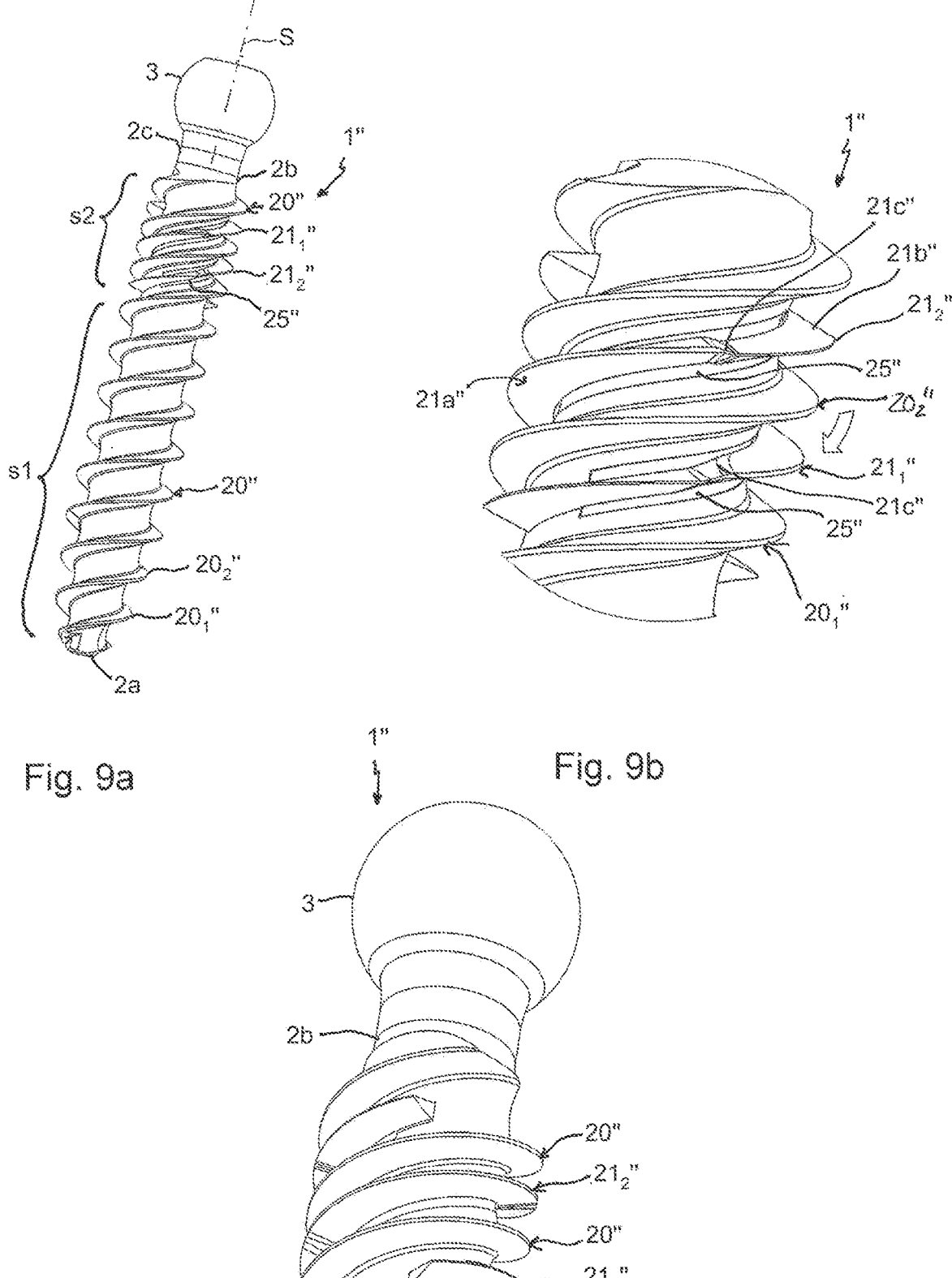
Figures 11A, 11B, 12A, 12B:
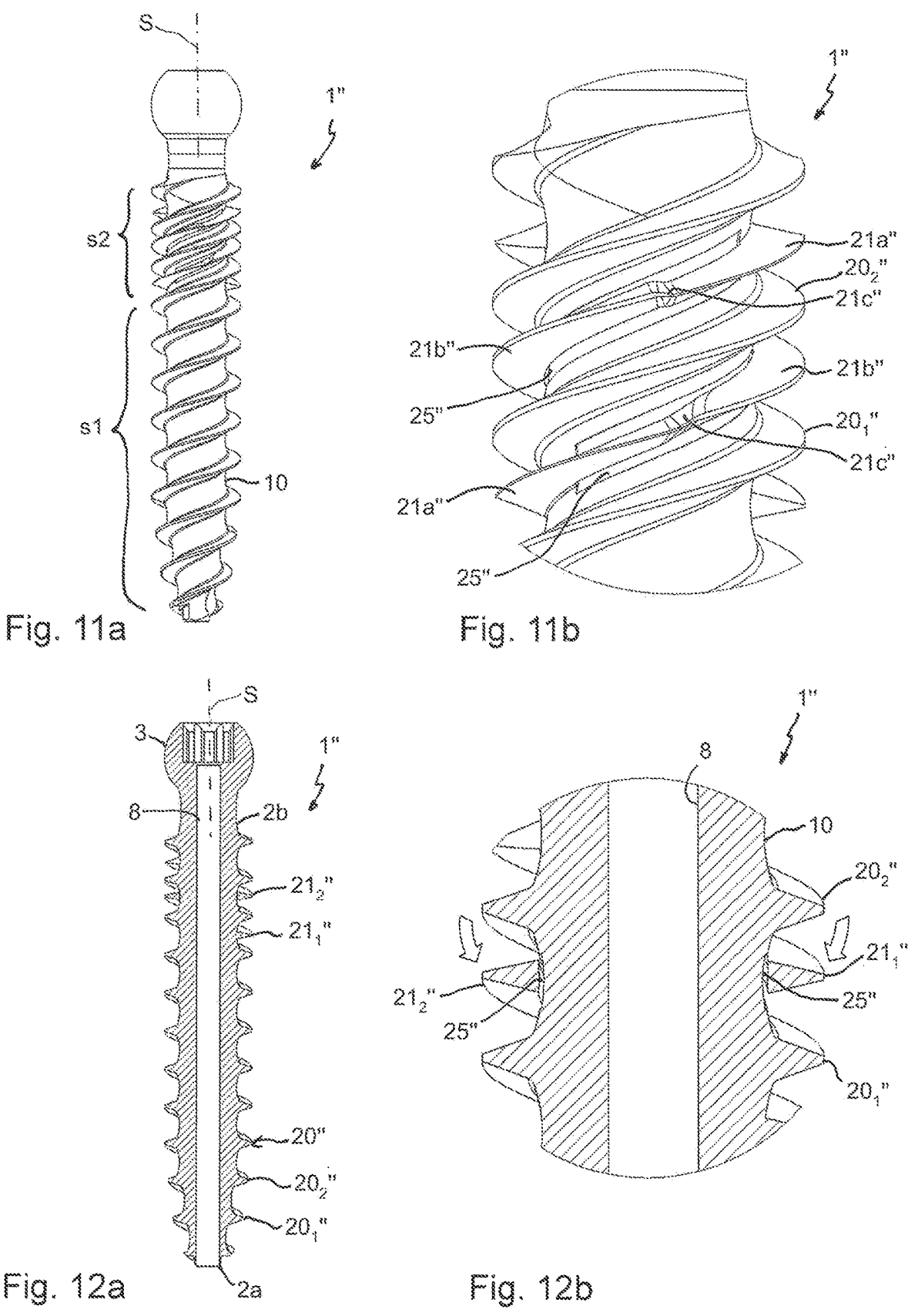

Referring to FIGS. 6 to 8b, a bone anchor 1' according to a second embodiment will be described. Parts and portions that are identical or similar to the bone anchor of the first embodiment are marked with the same reference numerals, and the descriptions thereof will not be repeated. The thread 20' of the first thread section s1 shown in this embodiment has a substantially sharp crest, and the thickness of the thread in the axial direction is smaller than that of the thread 20 according to the first embodiment. However, it shall be noted that the thread 20' may also have an identical regular thread shape as the thread 20 of the first embodiment. Also in this embodiment, the thread 20' that defines the regular thread shape is a double thread with two helices 20$_1$' and 20$_2$'. The additional thread structure includes a modified thread 21' in the second thread section s2 which lies on the same helix as the thread 20' of the first thread section s1, but which is bifurcated by a slit 22' into an upper helix 21b' and a lower helix 21a'. Moreover, the additional thread structure also has a helical recess 25' in the core 10 that may have substantially the same helical extension as the slit 22'. As best seen in FIG. 8b, the helical recess 25' extends under the upper helix 21b' and the lower helix 21a', such that they are separated from the core 10. By means of this, the upper helix 21b' and the lower helix 21a' may be partially resilient with respect to the core 10 in the region where the recess 25' is, where the recess 25' forms an undercut.

The thickness of the thread 21' formed by the helices 21b' and 21a' in the axial direction is greater than that of the thread 20' of the first thread section s1. In other words, the helix of the modified thread 21' is thickened compared to the helix of the thread 20'. The shape and size of the slit 22' is selected such that the lower helix 21a' is flexible relative to the upper helix 21b'. In the embodiment, the additional thread structure in the form of the modified thread 21' includes a lower step 26a where the thickened portion begins and that is located closer to the first end 2a of the shank, and ends with an upper step 2b where the thickened portion stops and that is located closer to the second end 2b of the shank 2. As depicted in FIG. 7b, since each of the two helices 20$_1$' and 20$_2$' has the modified thread 21', the visible step 26a in FIG. 7b belongs to the beginning of the thickened portion of the helix 20$_1$', while the visible step 26b in FIG. 7b belongs to the end of the thickened portion of the helix 20$_2$'. Moreover, the thickened portion of the first helix 20$_1$' is offset from the thickened portion of the second helix 20$_2$' of the double thread. The helical slit 22 begins before the lower step 26a in the helical path closer to the first end 2a, and ends beyond the upper step 26b in the direction of the helical path closer to the second end 2b. An axial coverage of the modified thread 21' is preferably about half a turn, but can be less or more up to about one turn.

Adjacent to the neck 2c, a small axial portion of the thread 20' with the regular thread shape may be present, as can be seen in FIG. 7a.

In use, when the additional thread structure including the bifurcated thread 21' enters the bone, preferably the cortical bone region, the upper helix 21b' and the lower helix 21a' are pressed together or towards one another. This is caused by the increased thickness of the modified thread 21' in the second thread section s2 and the flexibility of the helices 21b' and 21a' due to the slit 22'. In addition, the helices 21b' and 21a' can resiliently flex to some extent with regard to the core 10. Thereby, the two helices 21b' and 21a' may be tensioned or pre-loaded against each other and also against the bone, which results in an additional holding force of the bone anchor in the bone. Also, the slit 22' and the recess 25' may provide space for ingrowth of bone material that further reduces the risk of loosening.

Referring to FIGS. 9a to 12b, a bone anchor 1" according to a third embodiment will be described. Parts and portions of the third embodiment that are identical or similar to the previous embodiments are marked with the same reference numerals, and the descriptions thereof will not be repeated. The thread 20" that defines the regular thread shape may be identical to the thread 20' of the second embodiment. However, the thread 20" may also be identical to the thread 20 of the first embodiment. The additional thread structure includes two additional helices 21$_1$" and 21$_2$" in the second section s2 that run between the two helices 20"$_1$ and 20"$_2$ of the thread 20". The additional helices 21$_1$" and 21$_2$" have thread entries that are offset from each other by 180°. Each additional helix 21$_1$", 21$_2$" includes two differently arranged portions. A first portion 21a" extends axially in the middle between the helices 20$_1$" and 20$_2$" of the thread 20". A second portion 21b" that is closer to the second end 2b than the first portion 21a" is to the second end 2b in the axial direction is slightly shifted towards the second end $2b$ of the shank 2. The second portion 21$b$" preferably extends along a half turn of each of the helices 21$_1$", 21$_2$". The first portion 21$a$" and the second portion 21$b$" taper towards a transition portion 21$c$", where they join each other. Adjacent to the second portion 21$b$" towards the second end $2b$ of the shank 2, another transition portion 21$c$" may be formed that is again located in the middle between the helices 20$_2$" and 20$_1$" like the first portion 21$a$". The first helix portion 21$a$" and the second helix portion 21$b$" of one additional helix 21$_1$" are arranged offset from those of the second additional helix 21$_2$", preferably in a manner such that the first and second portions alternate from one helix to the next helix.

Furthermore, the additional thread structure includes helix-shaped recesses or undercuts 25" in the core 10 that extend under the additional helices 21$_1$" and 21$_2$", at least in portions thereof such that the additional helices 21$_1$" and 21$_2$" are partially separated from the core 10. The helix-shaped recesses 25" in the core cover at least a region along the second portion 21$b$", and preferably also extend partially under the first portion 21$a$". By means of these recesses 25", the modified thread 21" is flexible to some extent with respect to the core 10.

It should be noted that the second thread section s2 may cover several turns of the thread 20". In such a case, first portions 21$a$" and second portions 21$b$" and the corresponding helix-shaped recesses 25" are arranged one after the other in an alternating manner, and are joined by thinner transition portions 21$c$". The thickness of the additional helices may be smaller than the thickness of the helices of the thread 20".

In use, as depicted in particular in FIG. 12$b$, when the additional thread structure engages the bone, in particular the cortical bone, the second portions 21$b$" of the additional helices, that form a type of ramp, experience a force with a downward component, as indicated by the arrows, that generates a pre-load that enhances the holding force. Moreover, the resistance against loosening, screwing out, or pull-out may be increased.

Figure 13:
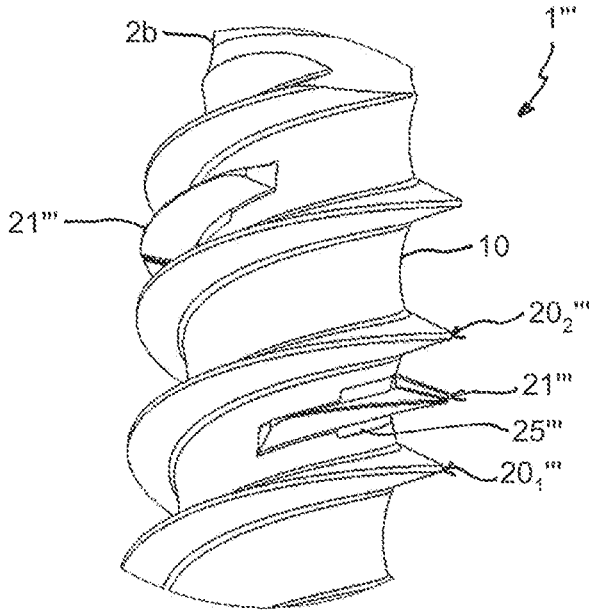
FIG. 13 shows a perspective view of a portion of a shank of a bone anchor according to a fourth embodiment.
Figure 14A:
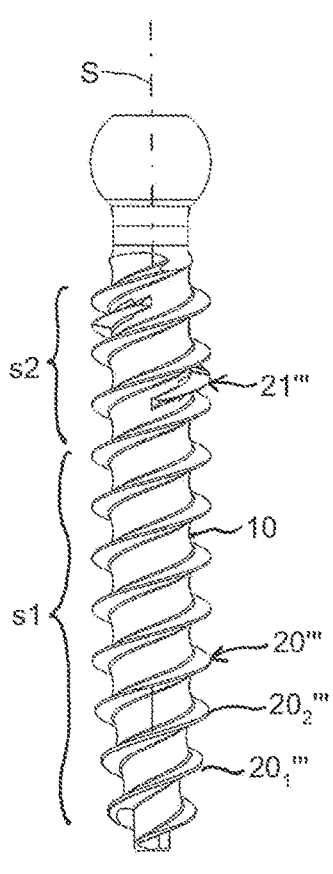
FIG. 14a shows a side view of the bone anchor of FIG. 13.
Figure 14B:
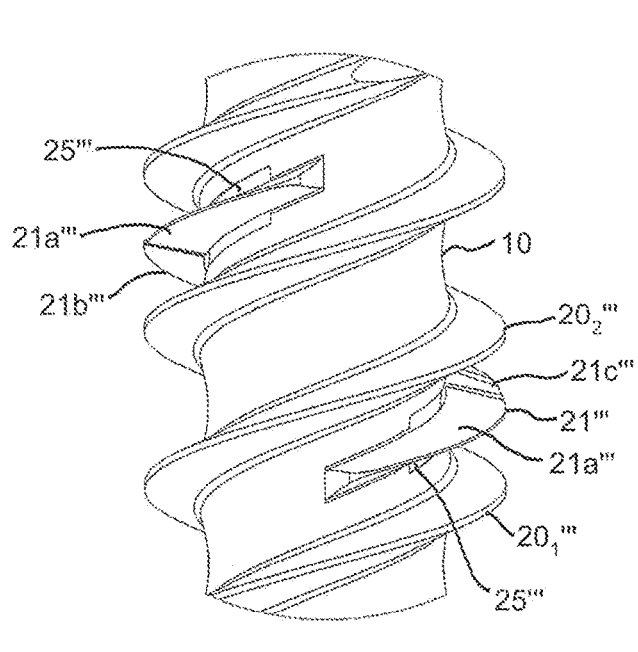
Figure 15A:
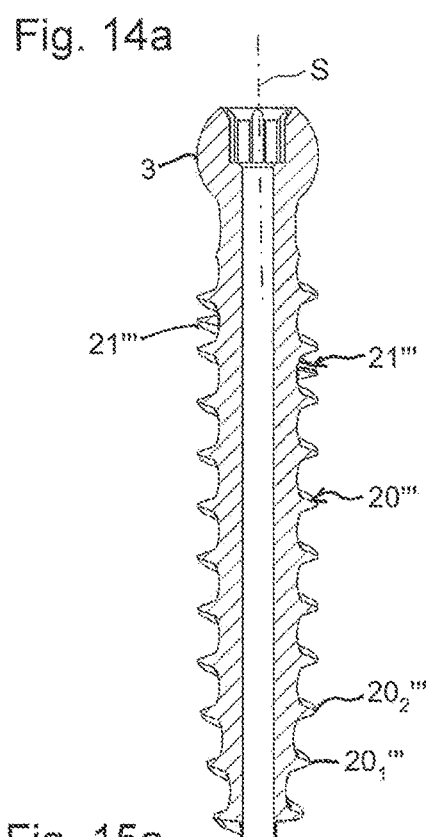
FIG. 15a shows a cross-sectional view of the bone anchor of FIGS. 13 to 14b, the cross-section taken in a plane including the shank axis and extending through a center of a head of the bone anchor.
Figure 15B:
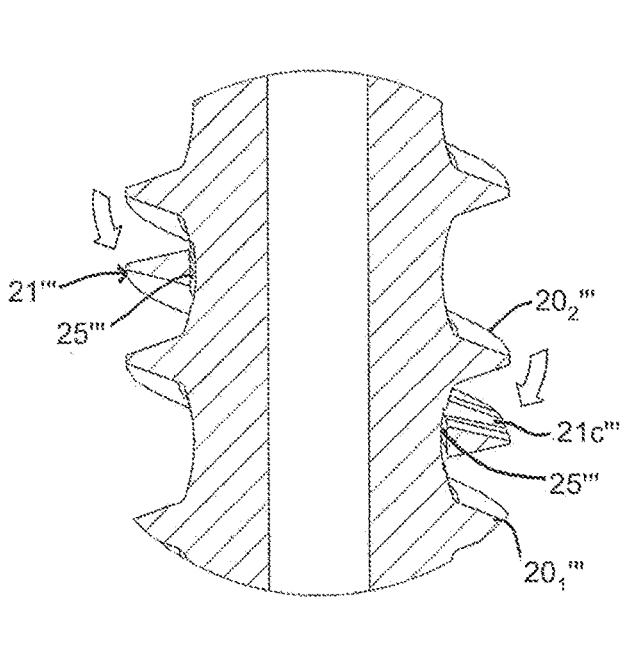

Referring to FIGS. 13 to 15$b$, a bone anchor 1''' according to a fourth embodiment will be described. Parts and portions of the bone anchor according to the fourth embodiment that are identical or similar to those of the previous embodiments are marked with the same reference numerals, and the descriptions thereof will not be repeated. The bone anchor 1''' according to the fourth embodiment differs from the bone anchor 1" according to the third embodiment in that the additional thread structure includes a single additional helix 21''' that runs between two turns 20$_1$''' and 20$_2$''' of the thread 20''' and a recess or undercut 25''' that separates at least a portion of the additional helix 21''' from the core 10. The structure of the single additional helix 21''' is the same as one of the additional helices 21$_1$" and 21$_2$" of the third embodiment.

In use, as shown in FIG. 15$b$, when the bone anchor according to the fourth embodiment is inserted into bone and the second section s2 engages the cortical bone, a downward force as depicted with the arrows is generated onto the additional helix 21'''. This may result in a tension or pre-load between the flanks of the additional helix and the bone that may increase the holding force. Moreover, this may increase a resistance against loosening, screwing back, or pull-out.

Figure 16A:
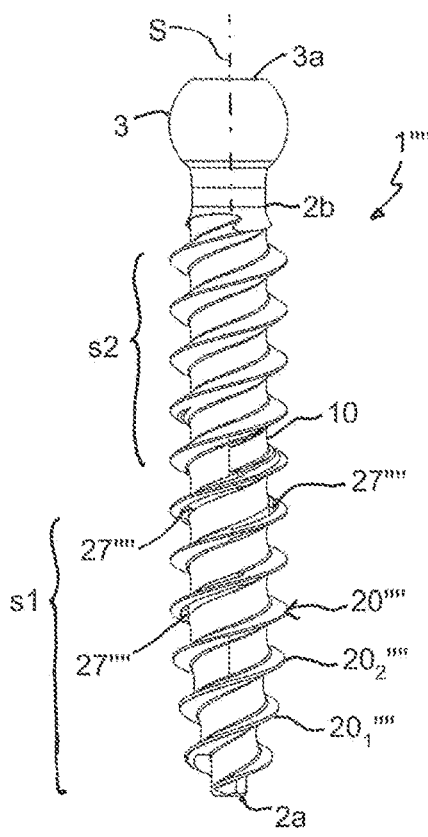
FIG. 16a shows a side view of a bone anchor according to a fifth embodiment.
Figure 16B:
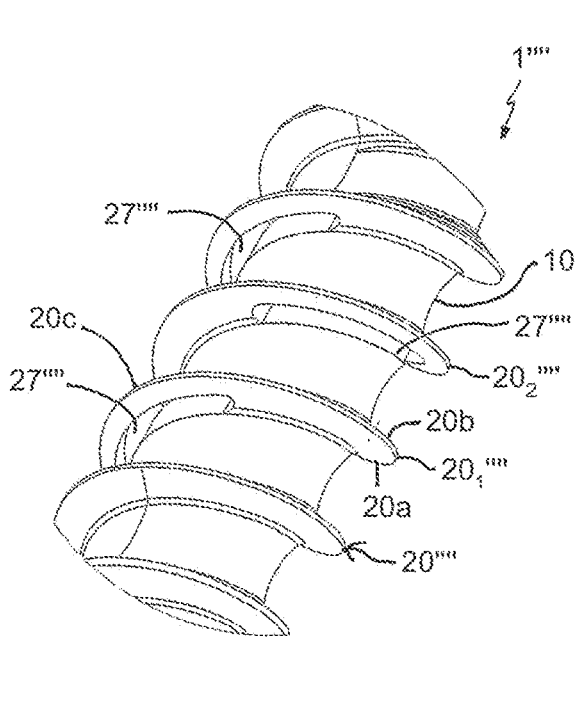
Figure 17A:
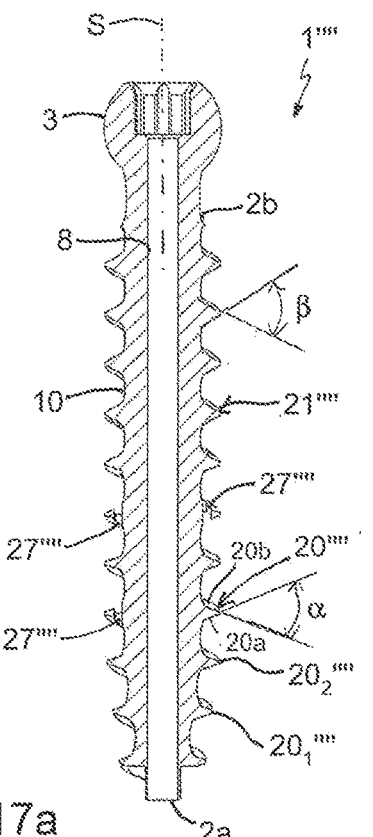
FIG. 17a shows a cross-sectional view of the bone anchor of FIGS. 16a and 16b, the cross-section taken in a plane including the shank axis and extending through a center of a head of the bone anchor.
Figure 17B:
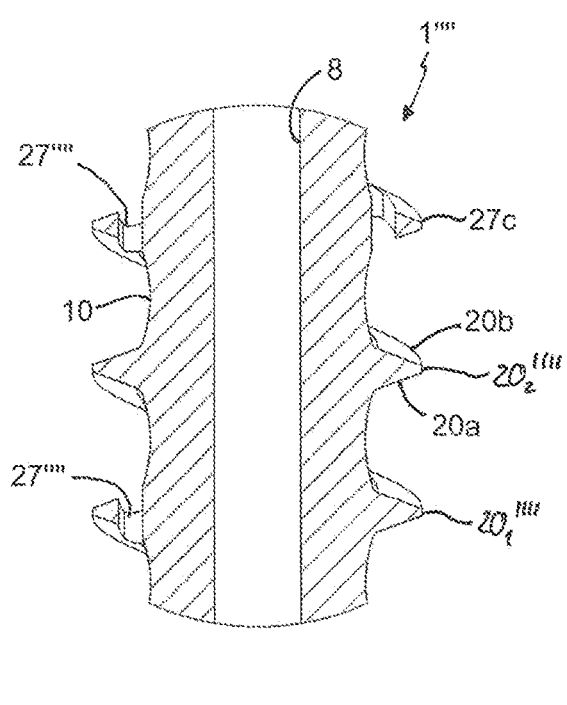

Referring to FIGS. 16$a$ to 17$b$, a bone anchor 1'''' according to a fifth embodiment of the bone anchor is shown. Parts and portions of the bone anchor 1'''' according to the fifth embodiment that are identical or similar to parts and portions of the previous embodiments are marked with the same reference numerals, and the descriptions thereof will not be repeated. The bone anchor 1'''' according to the fifth embodiment includes a thread 20'''' which is a double thread having a first helix 20$_1$'''' and a second helix 20$_2$'''' similar to that of the third embodiment in a first thread section s1 adjacent to the first end $2a$ of the shank 2. The lower flank 20$a$ and the upper flank 20$b$ form an angle $\alpha$ which is shown in FIG. 17$a$ only schematically. The shank 2 further includes a second thread section s2 that covers the shank from an end of the first thread section s1 up to the second end $2b$ and in which an additional thread structure with a modified thread 21'''' is provided. The thread 21'''' is modified such that the lower flank 21$a$'''' and the upper flank 21$b$'''' form a second angle $\beta$ that is greater than the first angle $\alpha$ of the thread 20''''. Thereby, the thickness of the thread is increased. This also enhances the holding force, particularly in the cortical bone.

A still further additional thread structure is formed by a plurality of at least partially helix-shaped recesses 27'''' in the first thread section s1, i.e., in the helices 20$_1$'''' and 20$_2$''''. The recesses 27'''' extend in the axial direction entirely through the thread from the upper flank 20$b$ to the lower flank 20$a$. The recesses 27'''' are elongate and follow the helical course of the thread 20''''. A length of the recesses 27'''' may be about a quarter of a turn. The crest 27$c$ in the region of the recesses 27'''' remains intact. Thus, the recesses 27'''' are closed in the radially outward direction. In each of the helices 20$_1$'''' and 20$_2$'''', at least one single recess 27'''' may be formed, wherein the positions of the recesses are offset from each other from one helix to the other.

In use, the additional thread structure in the form of the increased thickness of the thread provides for an enhanced holding force. The additional thread structure in the form of the recesses may allow an increased ingrowth of bone material. As the position of the recesses 27'''' is closer to the middle of the shank of the bone anchor, the additional thread structure enhances the holding force, in particular, in cancellous bone.

Referring to FIGS. 18$a$ to 19$b$, a bone anchor 100 according to a sixth embodiment will be described. Parts and portions of the bone anchor according to the sixth embodiment that are identical or similar to parts and portions of the bone anchors according to the previous embodiments are marked with the same reference numerals, and the descriptions thereof will not be repeated. The bone anchor 100 according to the sixth embodiment differs in some aspects from the bone anchors according to the previous embodiments. The bone anchor includes a thread 200 that defines the regular thread shape and which is present in the first thread section s1. In the embodiment shown, the thread 200 is a double thread with a first helix 200$_1$ a second helix 200$_2$. In the first thread section s1, the upper flank 20$b$ and the lower flank 20$a$ form an angle $\alpha$. In the second thread section s2, the thread 200 is modified to a double thread 210 having two helices 210$_1$, 210$_2$ which form the additional thread structure. The modified thread 210 forms an angle $\beta$ between the upper flank 210$b$ and the lower flank 210$a$ that is greater than the angle $\alpha$ of the thread 200 in the first section s1. Thus, the thickness of the modified thread 210 in the second section s2 is greater than the thickness of the thread 200 in the first section s1. Moreover, the crest 210$c$ may be more flat in the second section s2 compared to a more sharp crest in the first section s1.

Each of the helices in the second thread section s2 has a still further additional thread structure formed by at least one groove, preferably by two grooves 270$a$, 270$b$, that each extends along both the upper flank 210$b$ and the lower flank 210$a$ in a helical path. The outer groove 270$a$ that is positioned at a radial outer position, closer to the crest 210c, may have a greater width in a transverse direction compared to the inner groove 270b that is closer to the core 10. A transverse groove 270c may further be provided to radially connect the outer groove 270a to the inner groove 270b at the starting area of the thread 210 that is positioned closer to the first end 2a.

Figures 18A, 18B, 19A, 19B:
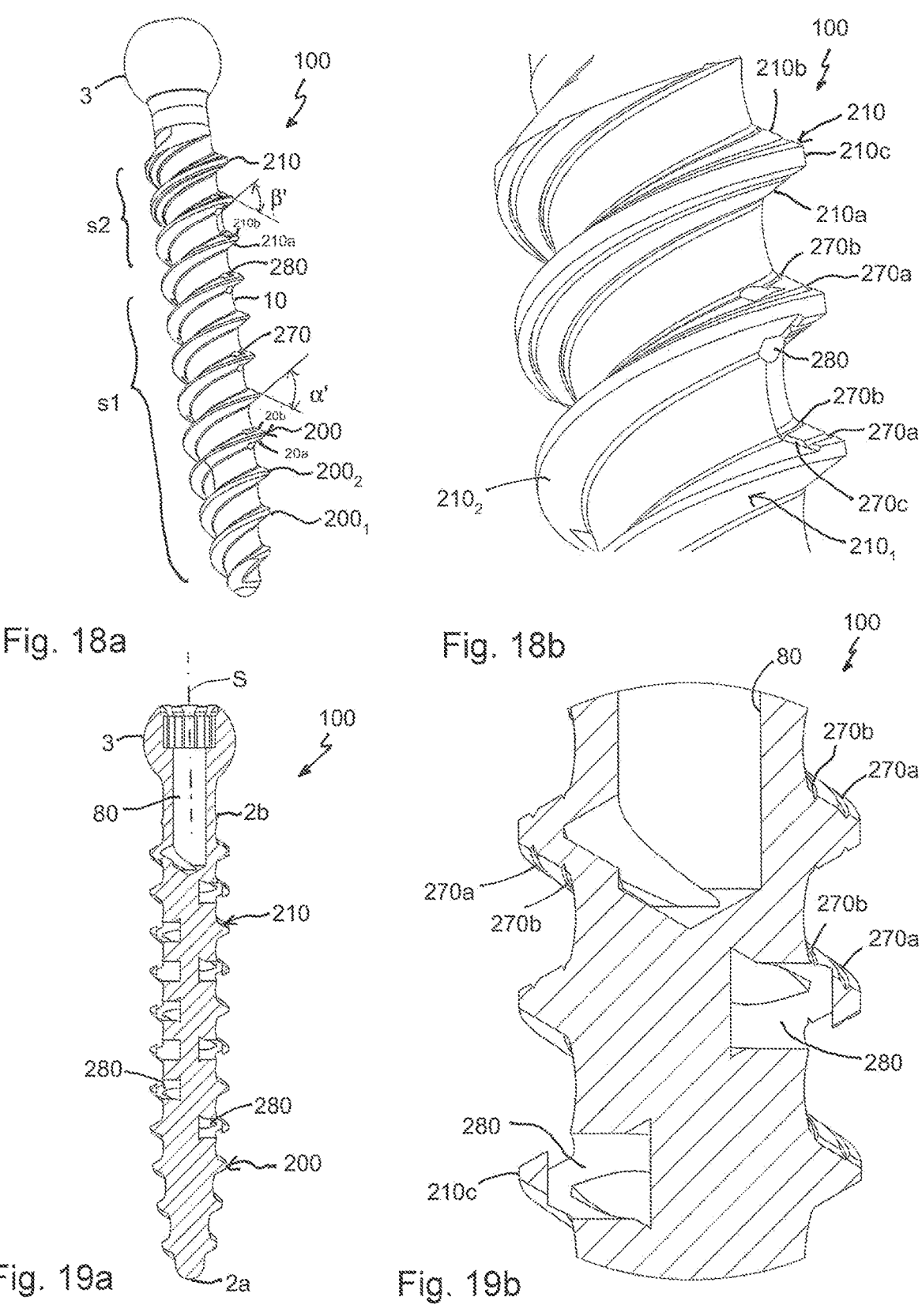

In addition, a plurality of recesses 280 extending substantially in the axial direction from the upper flank 20b to the lower flank 20a may be provided. The recesses 280 are provided along an axial region between a distance from the second end 2b in the second thread section s2 and a distance from the first end 2a in the first thread section s1. In greater detail, the recesses 280 may be arranged in at least one, and preferably two or more, axial rows offset from each other, as can be seen in FIGS. 19a and 19b. The shape of the recesses 280 may have a rounded inner part closer to the core 10 and a more flat outer part that is located still inside the thread flank. In other words, the recesses 280 are closed and do not interrupt the crest 210c. The number of the plurality of recesses 280 may be at least two, and preferably more than three, recesses in one axial row. Also, the axial distance of the recesses 280 in one row may be different from that of another other row, as depicted in FIG. 19a.

The bone anchor 100 has a short channel 80 that extends from the free end surface 3a of the head 3 to a distance therefrom into the shank.

In use, with the modified thread 210, the holding force can be increased due to the increased thickness of the modified thread 210. By means of the grooves 270, the ingrowth of bone material and tissue is promoted. As a result, the holding force of the screw within the bone can be increased, and/or the resistance against loosening, screwing out, or pull-out can be increased.

It shall be noted, that all embodiments of the bone anchor are preferably made by an additive manufacturing method as explained with respect to the first embodiment.

Further modifications of bone anchors according to embodiments of the invention may be conceivable. The features of the various bone anchors can be mixed and matched to produce a variety of further embodiments. The shape of the bone anchor is not limited to the detailed shape shown in the embodiments. For example, various designs of the tips of the bone anchor may be conceivable. The head may have other shapes or can be omitted. Even the neck portion can be omitted. A suitable drive structure is then formed at the second end of the shank. The additional thread structure can be provided at various positions along the shank. Furthermore, more than one section with an additional thread structure may be provided on the shank, and the additional thread structures do not need to be identical on one shank.

It should be noted that the core may also be tapered and narrow from the second end up to the first end of the shank, or its outer diameter may decrease in steps between the second end and the first end of the shank. In a further embodiment, the shank may be fenestrated, i.e., may have one or a plurality of openings that connect the channel laterally with the outside of the bone anchor.

The threads that form the regular thread shape may also be a single thread or a multiple thread with more than two thread entries. The thread or threads may also have any thread shape that is suitable for anchoring in bone.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A bone anchor comprising a shank configured to be anchored in bone, the shank having a first end configured to be inserted first into the bone, an opposite second end, and a longitudinal axis extending through the first end and the second end, the shank comprising:
   a core;
   a thread configured to engage the bone, wherein the thread extends in a helix around the core and comprises a lower flank directed towards the first end and an upper flank directed towards the second end, wherein the upper flank and the lower flank define a first cross-sectional thread shape; and
   an additional thread structure comprising a cavity that extends together with part of the thread in the helix around the core, wherein the thread and the additional thread structure together define a second cross-sectional thread shape that is different from the first cross-sectional thread shape, and wherein an axial length of the portion of the thread that has only the first cross-sectional thread shape is greater than an axial length of the entire portion of the thread that includes the second cross-sectional thread shape.

2. The bone anchor of claim 1, wherein the additional thread structure is closer to the second end of the shank than to the first end of the shank.

3. The bone anchor of claim 1, wherein the cavity is configured to render the thread at least partially flexible.

4. The bone anchor of claim 1, wherein the cavity is formed by a helix-shaped slit that separates the upper flank and the lower flank from each other.

5. The bone anchor of claim 4, wherein the lower flank in the second cross-sectional thread shape is offset towards the first end compared to the lower flank of the first cross-sectional thread shape.

6. The bone anchor of claim 4, wherein the helix-shaped slit renders at least one of the upper flank or the lower flank axially resilient relative to the other flank.

7. The bone anchor of claim 1, wherein the additional thread structure further comprises one or more transverse slits in the upper flank and/or the lower flank.

8. The bone anchor of claim 1, wherein the cavity is formed by a recess that extends into the core and that radially separates at least a portion of the thread from other portions of the core.

9. The bone anchor of claim 1, wherein the second cross-sectional thread shape is thicker in the axial direction than the first cross-sectional thread shape.

10. The bone anchor of claim 1, wherein the second cross-sectional thread shape comprises a section that is offset towards the second end when compared to the first cross-sectional thread shape.

11. The bone anchor of claim 1, wherein the cavity is formed by at least one aperture in the thread that extends in an axial direction fully from the upper flank to the lower flank, and wherein a crest of the thread in the region around the aperture remains intact.

12. The bone anchor of claim 11, wherein the at least one aperture comprises a plurality of apertures.

13. The bone anchor of claim 12, wherein the plurality of apertures do not overlap in the axial direction.

14. The bone anchor of claim 1, wherein the cavity is formed by at least one groove extending helically in the upper flank and/or in the lower flank.

15. The bone anchor of claim 1, wherein the thread is a multiple thread.

16. The bone anchor of claim 1, wherein the shank is manufactured using an additive manufacturing method.

17. The bone anchor of claim 1, wherein the cavity extends continuously around the core for more than half a turn of the helix.

18. A bone anchor comprising a shank configured to be anchored in bone, the shank having a first end configured to be inserted first into the bone, an opposite second end, and a longitudinal axis extending through the first end and the second end, the shank comprising:

a core;

a thread configured to engage the bone, wherein the thread extends in a helix around the core and comprises a lower flank directed towards the first end, an upper flank directed towards the second end, and a crest between the lower and upper flanks; and an additional thread structure comprising a cavity formed in the crest that extends together with part of the thread in the helix around the core, wherein the cavity extends radially from the crest to a radial position that corresponds substantially to the core, and wherein part of the crest remains axially between the cavity and the upper flank and/or between the cavity and the lower flank.

19. The bone anchor of claim 18, wherein the cavity renders at least one of the upper flank or the lower flank axially resilient relative to the other flank.

20. A bone anchor comprising a shank configured to be anchored in bone, the shank having a first end configured to be inserted first into the bone, an opposite second end, and a longitudinal axis extending through the first end and the second end, the shank comprising:

a core;

a thread configured to engage the bone, wherein the thread extends in a helix around the core and comprises a lower flank directed towards the first end and an upper flank directed towards the second end; and an additional thread structure comprising a cavity formed into the core that extends together with part of the thread in the helix around other portions of the core, wherein the cavity radially separates at least a portion of the thread from the other portions of the core.

\* \* \* \* \*